United States Patent
Kabaha et al.

(10) Patent No.: US 9,586,213 B2
(45) Date of Patent: Mar. 7, 2017

(54) CENTRIFUGATION CHAMBER WITH DEFLECTORS

(71) Applicant: Miltenyi Biotec GmbH, Bergisch-Gladbach (DE)

(72) Inventors: Eiad Kabaha, Bergisch Gladbach (DE); Ralf-Peter Peters, Bergisch Gladbach (DE); Stefan Miltenyi, Bergisch-Gladbach (DE); Juliane Stuth, Bergisch Gladbach (DE)

(73) Assignee: Miltenyi Biotec GmbH, Bergisch-Gladbach (DE)

( * ) Notice: Subject to any disclaimer, the term of this patent is extended or adjusted under 35 U.S.C. 154(b) by 666 days.

(21) Appl. No.: 13/868,915

(22) Filed: Apr. 23, 2013

(65) Prior Publication Data

US 2013/0310241 A1    Nov. 21, 2013

(30) Foreign Application Priority Data

May 15, 2012    (EP) .................................... 12168083

(51) Int. Cl.
*B04B 1/02*    (2006.01)
*B04B 5/04*    (2006.01)
(Continued)

(52) U.S. Cl.
CPC ............... *B04B 11/00* (2013.01); *B04B 1/02* (2013.01); *B04B 5/0442* (2013.01); *B04B 11/06* (2013.01)

(58) Field of Classification Search
CPC   B04B 1/02; B04B 11/00; B04B 11/06; B04B 5/0442
(Continued)

(56) References Cited

U.S. PATENT DOCUMENTS 4,109,854 A * 8/1978 Brown .................. B04B 5/0442
494/18
4,708,712 A * 11/1987 Mulzet .................. B04B 5/0442
494/45
(Continued)

FOREIGN PATENT DOCUMENTS

EP           0 869 838 B1   10/1998
WO     WO-2009/072003 A2    6/2009
(Continued)

OTHER PUBLICATIONS

European Search Report and European Search Opinion mailed on Oct. 16, 2012, for European Patent Application No. 12168083.9, filed on May 15, 2012, six pages.

*Primary Examiner* — Charles Cooley
*Assistant Examiner* — Shuyi S Liu
(74) *Attorney, Agent, or Firm* — Morrison & Foerster LLP (57) ABSTRACT

A centrifuge chamber for separating a sample into at least two components, including a cylinder having a base plate and a cover plate, and a rotational axis assembly having at least one port for input and/or output of the sample, the port being connected to a tube located on or in the base plate and/or cover plate, and the tube having one or more openings into the centrifuge chamber, where at least one opening of the tube is provided with at least one flat-shaped deflector having a surface lying substantially parallel with the cylinder, and a width at its base of at most $1/10$ of the inner circumference of the cylinder.

12 Claims, 8 Drawing Sheets (51) Int. Cl.
*B04B 11/06* (2006.01)
*B04B 11/00* (2006.01)

(58) Field of Classification Search
USPC .......................................................... 494/56
See application file for complete search history.

(56) References Cited

U.S. PATENT DOCUMENTS

| | | | | |
|---|---|---|---|---|
| 5,837,150 | A * | 11/1998 | Langley | A61M 1/3624 210/782 |
| 5,879,280 | A * | 3/1999 | Hlavinka | B04B 5/0442 494/10 |
| 2007/0102374 | A1* | 5/2007 | Kolenbrander | A61M 1/3693 210/787 |
| 2008/0015099 | A1* | 1/2008 | Heinrich | B04B 1/08 494/68 |
| 2011/0215044 | A1* | 9/2011 | MacKel | B04B 11/06 210/403 |
| 2015/0017714 | A1* | 1/2015 | Kabaha | C12M 23/24 435/297.3 |

FOREIGN PATENT DOCUMENTS

| | | | |
|---|---|---|---|
| WO | WO-2009/072003 A3 | 6/2009 | |
| WO | WO-2009/072006 A2 | 6/2009 | |
| WO | WO-2009/072006 A3 | 6/2009 | |
| WO | WO 2009072006 A2 * | 6/2009 | ......... A61M 1/3693 |

* cited by examiner

CENTRIFUGATION CHAMBER WITH DEFLECTORS

CROSS REFERENCE TO RELATED APPLICATIONS

This application claims priority to European Application No. 12168083.9 filed May 15, 2012, incorporated herein by reference in its entirety

FIELD OF THE INVENTION

This invention relates to a chamber for a centrifuge for separating a liquid biological sample into at least two components or fractions.

BACKGROUND OF THE INVENTION

Fractionation and separation of cells from suspensions such as blood or bone marrow is becoming more and more part of medical treatment. For such treatment, cells are extracted from a patient, then separated to provide the desired target cells, which are usually stimulated or manipulated or expanded before introducing into the same or a different patient. Extracting, preparation, fractionation, separation, manipulation and introducing of the cells should be performed as fast as possible to reduce stress imposed on the target cells and the patient. Optimally, the entire process is performed on-site at the patient.

Fractionation and separation of cell suspensions by centrifugation is long known in the art to separate samples of biological origin into two or more components. Centrifugation systems, especially centrifugation chambers can be optimised for the type of sample to be separated, for processing speed, separation quality or the amount of material to be processed.

For separation of cells from a suspension such as blood by centrifugation, it is beneficial to monitor the separation process and to provide the centrifugation chamber with appropriate input/output ports. In this respect, International Patent Applications WO 2009/072006 and WO 2009/072003 incorporated herein by reference in their entireties disclose a centrifugation system and a centrifugation chamber with means for controlling the separation process, and at least one input and output port located in the rotational axis of the centrifugation chamber. The centrifuge and chamber of WO 2009/072006 and WO 2009/072003 allow continuous centrifugation, wherein sample, media, gases and other materials can enter and leave the system e.g. through inlet and outlet ports without stopping the centrifugation process and refilling the centrifuge.

U.S. Pat. No. 5,837,150 discloses an apparatus comprising in inner and outer sidewall, wherein blood can be separated in a plurality of layers by centrifugation. The blood and the separated layers can enter and/or leave the chamber through openings of the inner sidewall, which are covered by shields located against the direction centrifugation. A centrifugation chamber with an inner and outer sidewall and openings in the inner sidewall is complicated to manufacture. Since the shields of the openings in the inner sidewall are located against the direction centrifugation, the speed of removal of liquids will be low.

U.S. Pat. No. 5,879,280 is directed to a centrifugation chamber with barriers to build up a pool of liquid which is drained for removal from the chamber. Building a pool of liquid will allow re-mixing of already separated layers ad poor separation quality will result. Furthermore, since the barriers are located against the direction centrifugation of flow, the speed of removal of liquid from the chamber will be low.

Any separation process by centrifugation involves at least the steps of providing a cell suspension into the centrifugation chamber, separation of the liquid into several layers according to their density and draining the separated layers from the chamber into different containers.

The quality of the separation step, i.e. the purity of the layers in the chamber, can be influenced by centrifugation time and applied gravity forces (i.e., the speed of rotation of the chamber).

Regardless of the purity of the layers during the centrifugation step, it was observed that separated layers were in part mixed again during draining of a layer, especially if the speed of draining is too high. Reducing the speed of draining would reduce re-mixing of adjacent layers but result in an undesired longer processing time.

Accordingly, there is a need to improve the centrifugation process in terms of processing speed and separation quality.

WO 2009/072006 discloses in FIG. 2A a centrifugation chamber with a deflector shield. The deflector shown has a width of about ⅓ of the circumference of the chamber. The purpose of this deflector is not described, but a deflector of this size prevents the separation of the sample into layers during centrifugation. The chamber as shown in FIG. 2A of WO 2009/072006 is not suitable for separation of samples into layers by centrifugal forces.

SUMMARY OF THE INVENTION

It is a goal of the invention to provide a centrifuge chamber for separating a sample into at least two components, including a cylinder having a base plate and a cover plate, and a rotational axis assembly defining at least one port for input and/or output of sample, the port being connected to a tube located on or in the base plate and/or cover plate and the tube having one or more openings into the centrifuge chamber, wherein at least one opening of the tube is provided with at least one flat-shaped deflector having a surface substantially parallel with the cylinder and a width at its base of at most ¹⁄₁₀ of the inner circumference of the cylinder.

The chamber according to the invention includes a circular base plate and a circular cover plate, both of which are oriented substantially perpendicular to a rotational axis assembly; and a cylinder or a wall which is oriented substantially perpendicular to the base and cover plate such that base plate, cover plate and cylinder can be glued or welded together in a water and gas-tight fashion. Thereby, a closed centrifugation chamber is formed, consisting of a pot-like bottom part and an upper part in the form of a lid.

Figure 1:
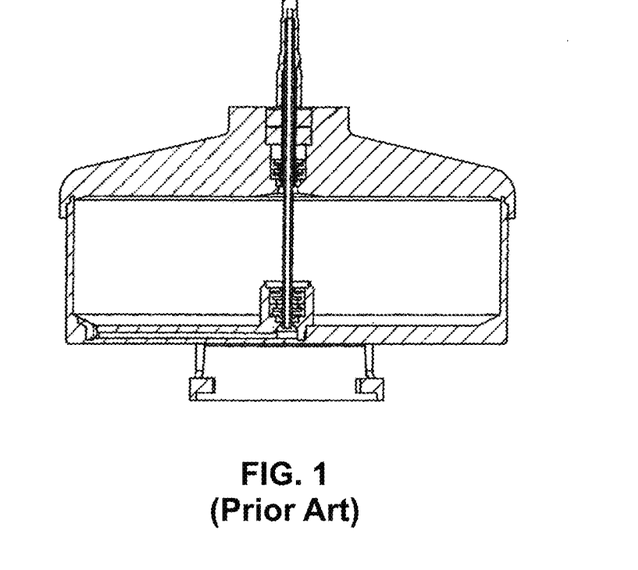
FIG. 1 shows a prior art centrifuge chamber.

FIG. 1 shows a standard centrifuge chamber known in the art, for example as disclosed in WO 2009/072006 or WO 2009/072003. This centrifuge chamber is provided with two input/output ports in the axis of the chamber connected via tubes to openings into the chamber. The chamber does not have deflectors shielding the openings.

Figure 2:
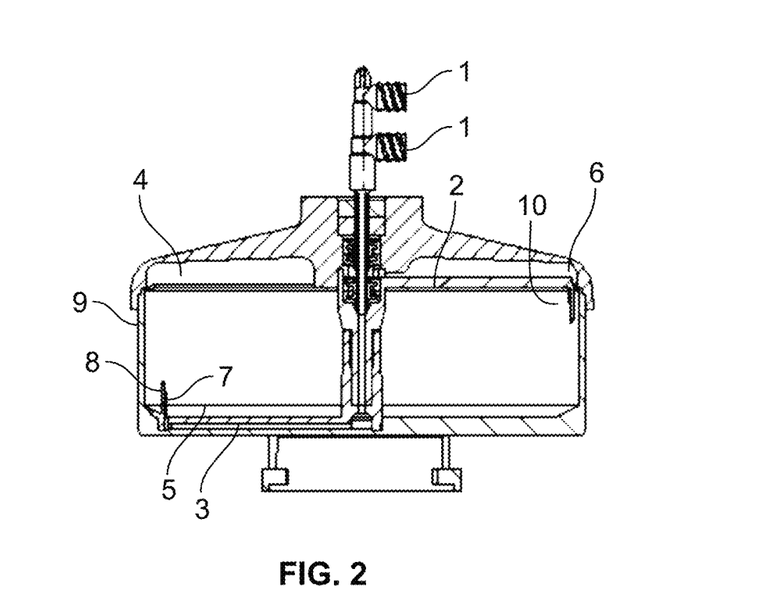
FIG. 2 shows a centrifuge chamber in accordance with the invention, in cross-section.

FIG. 2 shows a centrifugation chamber according to the invention. This chamber includes similar to the chamber as depicted in FIG. 1 two input/output ports in the axis assembly of the chamber, connected to tubes embedded in the base and cover plate, and ending in openings into the chamber. The openings of the base and cover plates are provided with deflectors, reducing unwanted remixing of liquid during draining of the chamber.

The centrifugation chamber according to the invention is suited to enhance and/or accelerate the physical separation of a sample into two or more components or to fractionate the sample into different layers and finally into different containers. The sample is preferably a biological sample, such as blood, bone marrow aspirate, leukapheresis samples, cells or compositions comprising cells or cellular components or alike.

The chamber according to the invention can for example be used in the following exemplary processes:

Reducing the volume of a sample by at least partially draining of undesired fraction or layer of the sample.

Separating a sample into layers having different density and removal of the layers from the chamber into different containers, for example separating blood or bone marrow into different fractions.

Washing of separated or non-separated cells for example with buffer media and subsequently separate the washed cells from the media and discharging the washing liquid.

Separation of cells by adding additives such as Ficoll or Percoll to provide a density gradient preparation.

Concentration of a sample preparation by removal of liquid.

Sample preparation previous to separation by centrifugation, magnetic and/or immunologic and/or fluorescence flow separation.

Cell processing such as cell activation, cell proliferation, cell transfection, cell staining followed or subsequently to a separation or washing step.

The chamber according to the invention is especially suited for the following processes:

Isolating leucocytes by separating and discharging erythrocytes and plasma from human blood.

Isolating certain subpopulations of leucocytes, for example leucocytes having one or more of the following surface marker CD4, CD8, CD25, CD 34 and/or CD 133 by separating leucocytes from human blood with subsequent cell labeling.

Preparation of leucocytes by discharging erythrocytes and plasma from human blood followed by one or more washing steps with cell media and/or density gradient additives.

Isolating, enriching or depleting cells having one or more of the following surface marker CD4, CD8, CD25, CD 34 and/or CD 133 from human blood for use in regenerative medicine, peripheral artery, liver disease or cardiac stem cell therapy.

Cytokine capture systems.

DETAILED DESCRIPTION OF THE INVENTION

A centrifugation chamber according to the invention includes as shown in FIG. 2, a rotational axis assembly with a rotating seal and preferably with two fluid lines or input/output ports 1. The centrifuge chamber includes furthermore a cover plate 4, a base plate 5 joined by cylinder 9. Cover plate 4 and base plate 5 are both provided with tubes 2, 3, which are connected to the respective input/output ports 1 and openings 6, 7 into the chamber. The openings 6, 7 are provided with deflectors 8, 10. Deflector 8 of the base plate 5 is located on tube 3 between the opening 7 of the tube and cylinder 9. Thereby, deflector 8 shields the opening 7 from the volume between the opening and cylinder 9 wall. Deflector 10 of the cover plate 4 is located between the opening 6 of tube 2 and the rotational axis assembly of the cylinder. Deflector 10 shields the opening 6 from the internal volume of cylinder 9.

In a first embodiment of the invention, at least one deflector is located between at least one opening of a tube and the cylinder. Located there, this deflector shields the opening from the volume between the opening and the cylinder and prevents, during draining of this volume, the unwanted sucking of liquid from another part of the chamber, i.e. from the volume between the opening and the cylinder 9 of the chamber. This embodiment is shown by opening 7 and deflector 8 in FIG. 2.

In a second embodiment, at least one deflector is located between at least one opening of a tube and the rotational axis assembly of the cylinder. Contrary to the first embodiment, this deflector shields the opening from the volume of the chamber between opening and cylinder wall and prevents sucking liquid from this volume when draining the internal volume of the chamber. This embodiment is shown by opening 6 and deflector 10 in FIG. 2.

In a third embodiment of the invention, the chamber includes deflectors at both locations of the first and second embodiments, i.e. at least one deflector is located between at least one opening of a first tube and the cylinder and at least one opening of a second tube and the rotational axis assembly of the cylinder. The location of the deflectors with respect to the openings and/or the distance to the cylinder can be the same or different. FIG. 2 shows this embodiment of the invention with openings 6,7 and deflectors 8,10 in FIG. 2.

Figure 3:
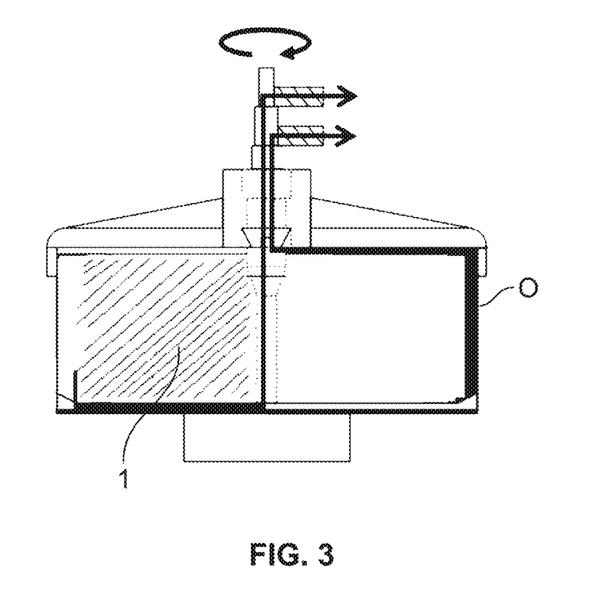
FIG. 3 shows detail of the fluid flow of the FIG. 2 chamber.

In the third embodiment of the invention, two openings of the chamber are connected or give access to two different volumes of the chamber and can be used to drain the liquid provided therein. FIG. 3 shows the respective line of flow and the volume of the chamber drained from which port and tube. The lower port on the rotational axis assembly drains the outside volume or layer O, whereas the upper port on the rotational axis assembly is connected to the inner volume I. With the shielding effect of the deflectors in accordance with the invention, re-mixing of the layers during draining is reduced, resulting in higher purity of the fractions obtained by draining the layers and/or the enablement of higher draining speed.

Preferably, the deflectors are located on the tubes. The centrifuge chamber according to the invention may include one to eight, ten or twelve tubes each having an opening with a deflector, preferably two or four tubes each having an opening with a deflector. The tubes and openings can be located all in the base plate, all in the cover plate or in the base and cover plates. If more than two tubes and openings are used, it is preferred to distribute the tubes and openings in a symmetrical way regardless if the tubes and openings are located in the base or cover plate. For example, a chamber with in total 4 tubes may have two tubes/openings located in the base plate and two in the cover plate oriented in a cross-wise manner, e.g., at a 90° angle.

The openings can be shaped as holes or line entries and their position in the centrifugation chamber can be configured such that they are best suited for the separation of a particular sample or for the draining of particular fluids in or out of the chamber. Depending on the components of a particular sample and the relative volume of each component in the sample, the openings can be positioned in a way that the fastest removal and/or detection of a particular layer can be achieved. In addition, the size of the openings can be optimized for the desired layer, for example in view of the size of the target cells and/or optimized volume flow.

Figure 4:
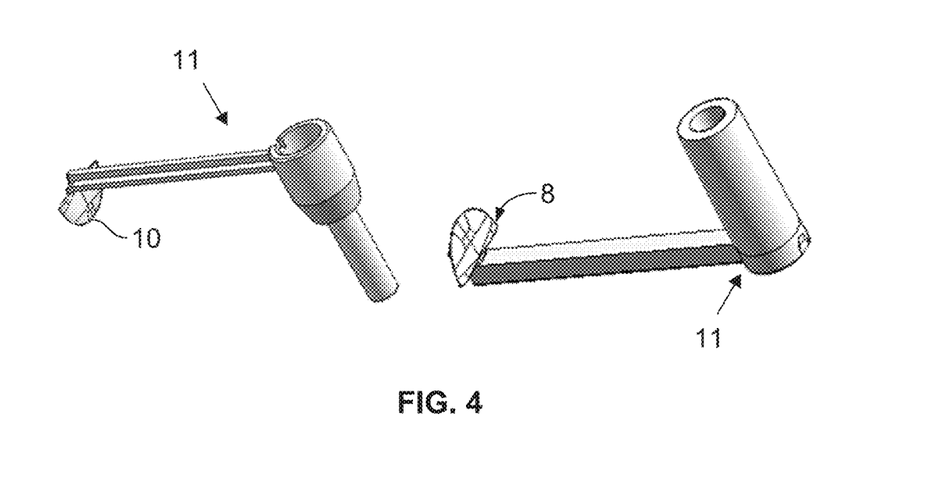
FIG. 4 shows deflectors with caps in accordance with the invention.

The deflector utilized in accordance with the present invention is flat-shaped, like a plate, and its surfaces lie substantially parallel with the cylinder wall, i.e. the deflector is bent in substantially the same curve radius as the cylinder wall. The shape of the deflector can be rectangular, triangular, half-round or elliptic. In one embodiment, the deflector has a broad base located at the opening of a tube and a smaller peak area in order to lower shear forces applied to the cells during centrifugation. The edges of the deflector should be chamfered to avoid cell losses by cutting or ripping of the cellular membrane at the edges. In one embodiment, the deflector is half-round or half-elliptic. FIG. 4 shows by way of example such deflectors 8,10 attached to caps 11 for closing of the channels.

The size of the deflectors should be sufficient to reduce the unwanted volume flow, for example volume drained from the part of the chamber located behind the opening in direction to the outside of the chamber when the draining of the part of the chamber located towards the rotational axis assembly is desired.

The size of the deflectors depends on the volume of the chamber, i.e. the larger the volume to be shielded, the larger the deflector should be and the intended draining speed. Regardless of its shape, the deflector should have a width at its base (at the opening of a tube) of $\frac{1}{10}$ to $\frac{1}{60}$, preferably of $\frac{1}{25}$ to $\frac{1}{40}$ of the inner circumference of the cylinder. For example, a cylinder having an inner diameter of 10 cm is provided with deflectors having a width at the base (at the opening of a tube) of 1 to 2 cm.

The height of the deflector is preferably the same or less than the width at its base, for example 50 to 95% of the width at the base. The deflector should be as thin as mechanically possible, but without exhibiting sharp edges which may damage or cut cells. Preferably, the thickness of the deflectors is between 0.5 and 2 mm.

The area of (one) surface of a deflector can be calculated or estimated from the given ranges in width and height, but is usually between 0.1 and 10 cm$^2$. In any case, the area of the deflector should not hamper the separation of the sample into layers but to reduce unwanted flow of liquid from the separated layers.

The chamber of the invention may include several such deflectors, which may have the same or different size and/or height and/or width.

FIGS. 2 and 3 show a chamber in a cross-sectional view with tubes or channels located in the base and cover plate of the chamber, each tube provided with a deflector. In this case, the opening and the deflector at the base plate are located 2 to 20 mm and the opening and the deflector at the cover plate are located 0.1 to 10 mm from the walls of the chamber. The location of the opening and the deflector define a residual volume of the chamber which is filled with liquid during centrifugation.

By adjusting the location of the opening and the deflector, i.e. adjusting the distance of the opening and the deflector to the cylinder, this residual volume can be adjusted to the needs of the desired separation process. For example, if a low residual volume is desired, the opening and the deflector should be located more towards the cylinder and vice versa. If the chamber has more than one opening with a deflector, the distances of the opening from the cylinder can be the same or different.

Figure 5:
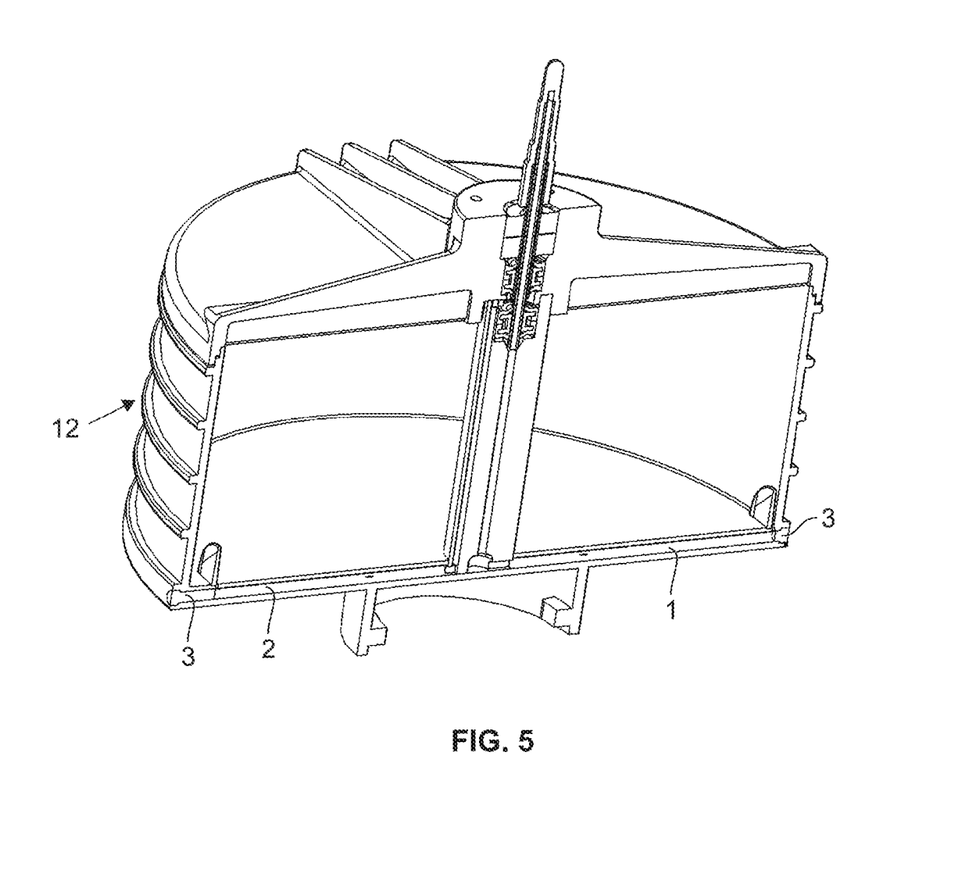
FIG. 5 shows a perspective view of another embodiment of the FIG. 2 chamber.

The openings and the deflectors can be provided at the base and/or cover plate depending on the needs of the separation process. In a further embodiment of the invention, the chamber is provided with two openings having a different distance from the cylinder at two different tubes leading to two different ports wherein each opening is provided with a deflector. An example where all the openings and tubes are located in the base plate and are connected to a different input/output is shown in FIG. 5.

Figure 6:
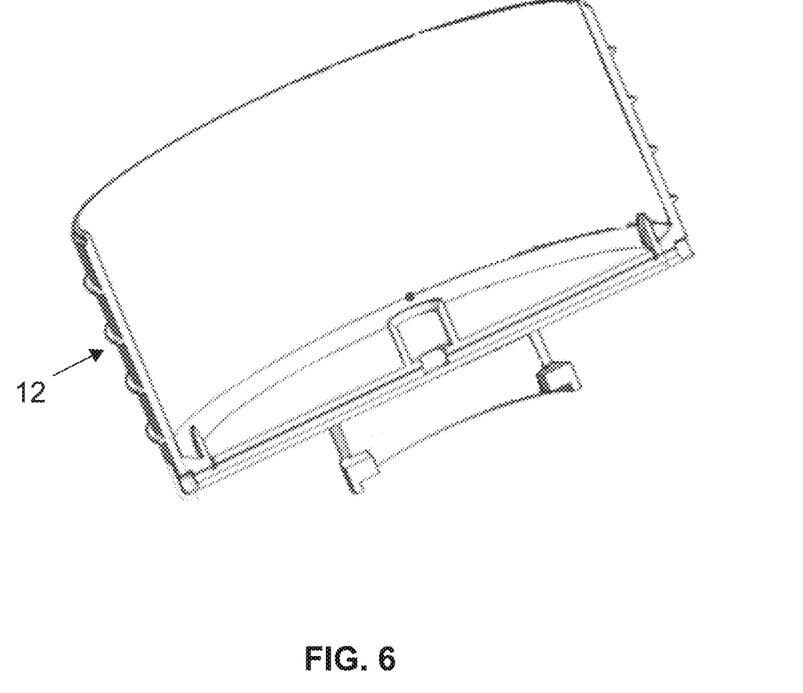
FIG. 6 shows yet another embodiment.

In yet another embodiment of the invention, the chamber is provided with two openings having the same distance from the cylinder at two different tubes leading into the same port where each opening is provided with a deflector. An example where all openings and tubes are located in the base plate and are connected to the same input or output port is shown in FIG. 6.

The chamber may include one or more of these combined tubes, for example two tubes and openings of the base plate may be connected to a first port and two tubes and openings of the cover plate may be connected to a second port, where the tubes of the base and cover plate are at a 90° angle with each other. The advantage of combined tubes is that a higher draining speed of the liquid from the chamber can be achieved.

The tubes can be embedded in the base plate and/or cover plate by providing channels in the base plate and/or cover plate which are covered by a cap 11. In this case, the deflector is preferably attached to the cap 11 during its manufacturing. FIG. 4 shows by way of example such caps 11 with deflectors 8,10. The caps 11 can be inserted into the channels in a water-tight provision, for example by appropriate glue or HF-welding. The caps 11 shown in FIG. 4 furthermore provide the rotational axis assembly A for the chamber including the tubing for output/input ports.

In an alternative embodiment of the invention, the tubes are not channels covered by caps 11, but bores defined in the base plate and/or cover plate, extending from the outside of the plate to the rotational axis assembly. This embodiment of the invention is shown in FIG. 5. The bores 1,2 are open to the outside of the chamber during manufacturing and need to be closed in a water and gas tight fashion, for example with plugs 3.

The chamber may have an inner diameter of 2 to 20 cm, preferably 8 to 15 cm and an inner height of 5 mm to 10 cm, preferably 2 to 7 cm. The total volume of the chamber can be between 10 and 2000 cm$^3$, preferably between 200 and 1000 cm$^3$.

Centrifugation is preferentially carried out between 10 and 2000×g, preferably between 100 and 500×g. In one embodiment, the chamber can be heated and cooled to provide for a temperature appropriate for the sample to be centrifuged. For this purpose, a heating and/or cooling mechanism or device can be located at the chamber or surrounding the chamber.

Figure 7:
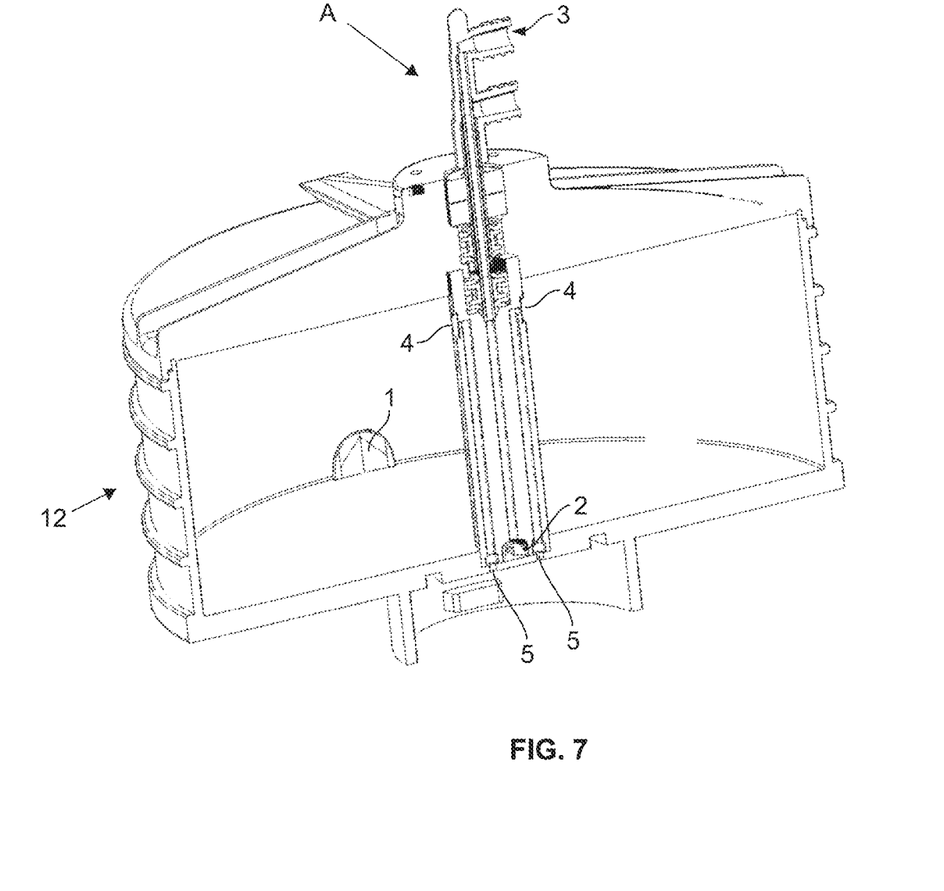
FIG. 7 shows yet another embodiment.

Since the chamber includes a circular base plate, a circular cover plate and a cylinder which are e.g. glued or welded or otherwise fastened together in a water and gas-tight fashion, the volume of a given chamber can be enlarged by using a higher cylinder with a cover or base plate having the same inner diameter. Chambers with enlarged volume can be filled with a higher volume of the sample, thereby putting a higher mass in motion resulting in higher forces acting on the cylinder walls. In order to provide sufficient mechanical stability of the chamber, especially when used with high load and high speeds of centrifugation, it is beneficial to provide the cylinder on its outside surface with one or more fins. A chamber carrying such fins 12 on its outside surface is shown in FIGS. 5, 6 and 7.

In a further embodiment of the invention, the chamber is provided with venting holes in the base and/or cover plate, where the venting holes are connected via venting tubes in the chamber's rotational axis assembly to the inner volume of the chamber. The venting tubes are preferably perpendicular to the lines connecting the openings provided with the deflectors and the input/output ports of the rotational axis. FIG. 7 shows this embodiment by way of example. Here, opening 1 is connected via tube 2 to the port 3. Venting holes 4 in the rotational axis assembly are open to the outside atmosphere of the chamber via tubes 6 to orifices in the base plate 5. Venting and/or gassing of the chamber can be performed by the orifices in the base plate even during centrifugation via the drive system (not shown).

The chamber has a cylinder, a base and a cover plate. The cylinder, base and cover plate can be round or circular to simplify production and to reduce any imbalance during the centrifugation process. In another embodiment, at least the cylinder may be shaped slightly elliptic, with a diameter in a first dimension being 0.5 to 10%, preferably 0.5 to 5% larger than in a second dimension orientated perpendicular to the first dimension. For example the cylinder may have in a first dimension a diameter of 120 mm and in a second dimension, being orientated perpendicular to the first dimension, a diameter of 122 mm.

The base and cover may have the same elliptic shape or can be round or circular. It is preferred that the tubes having openings with deflectors are oriented in the larger dimension of the elliptic cylinder. In this case, the cells will be moved by the force of centrifugation along the cylinder walls in the direction of the larger dimension of the cylinder i.e. in vicinity to the openings.

The chamber and caps and/or deflectors may be made of various materials such as ceramics, polystyrene (PS), polyethylene (PE), polypropylene (PP), polyvinylchloride, polycarbonate, glass, polyacrylate, polyacrylamide, polymethylmethacrylate (PMMA), and/or polyethylenterephtala (PET), polytetrafluorethylene (PTFE) and/or thermoplastic polyurethane (TPU), silicone or compositions comprising one or more of the above mentioned materials. Furthermore, the chamber may include or be made of biodegradable material such as collagen, chitin, alginate, and/or hyaluronic acid derivatives, polyactide (PLA), polyvinyl alcohol (PVA), olyglycolida (PGA) and their copolymers.

In a further embodiment, the chamber according to the invention includes a mechanism or device which controls the progress of the sample separation, and is positioned at the base plate or the cover plate of the chamber. The mechanism for controlling the progress of the sample separation is preferably positioned at a channel or at a gap located in the base plate or the cover plate of the chamber such that the sample can enter the channel or gap during the centrifugation and thus becomes detectable. Due to the centrifugal force, different components of the sample will form layers, which are detectable by light, for example with a camera or a light detector. Thereby, a signal is generated that allows for determining when the layer formation or sample separation is complete. Suitable mechanisms for controlling the progress of the sample separation are disclosed in WO 2009/072006 or WO 2009/072003 referred to above.

In another embodiment, the chamber is configured such that it can serve as or accommodate a container for cultivation of cells. Thereby, the centrifugation chamber can be used for cell separation processes, for cell culture purposes and for further processing of the cells grown therein. The chamber allows a large range of cell culture methods to be performed, such as growing of cells, separating, washing, enriching the cells or different kinds of cells, or others. For this purpose, the chamber may comprise further inlet/outlet openings, e.g. for gas, cell culture media or the like. Cell culture conditions are known in the art.

In a further embodiment, the centrifuge of the present invention can be part of a sample processing system, such as known from WO 2009/072006, WO 2009/072003 or European Patent EP 0 869 838 B1, which is hereby incorporated by reference in its entirety. The sample processing unit can be coupled to the input/output port of the centrifugation chamber and may comprise a separation column holder, a pump, a plurality of containers for (intermediate) storage of liquids during the separation process and a plurality of valves configured to at least partially control fluid flow through a fluid circuitry and a separation column positioned in the holder.

EXAMPLES

The enrichment of leukocytes from human bone marrow aspirate was investigated in order to isolate CD133+ hematopoietic stem and progenitor cells. Such cells are used for stem cell therapy like cardiac stem cell therapy, wherein the cells are first isolated from the bone marrow of a patient and then introduced into the heart muscle to the same patient. Since the introduction of cells into the heart muscle is performed during narcosis of the patient, isolation of the cells need to be with low cell losses and as fast as possible. Additional applications for enriched CD133+ cells are in the field of regenerative medicine, peripheral artery, and liver disease.

Centrifugation of whole blood was performed in a centrifugation chamber according to the invention and for comparison in a centrifugation chamber as shown in FIG. 1. Each chamber was part of a separation system as disclosed in WO 2009/072006 and was used to separate human blood into fractions comprising leukocytes, erythrocytes and plasma. The progress of the separation was monitored by a camera unit, which was installed above the centrifugation chamber.

Centrifugation Chamber

The chamber according to the invention used in the examples is shown in FIG. 2 and had an inner diameter of about 12 cm and in inner height of about 3.5 cm. The opening of the top channel is located at the periphery of the chamber, adjacent the outer wall (0.5 mm distance to the wall). The opening of the bottom channel was located a distance of about 6 mm to the outer wall, thereby providing a total volume between the opening of the bottom channel and the outer wall of about 70 ml. Both openings of the chamber were provided with half-round deflectors having a width at the base (at the openings) of about 1.5 cm and a height of about 1 cm. Both deflectors were slightly bent according to the curve radius of the cylinder and had the same size and shape.

A standard centrifugation chamber had the same dimensions, ports, channels and openings as described above, but is not provided with deflectors, for example as shown in FIG. 1 or disclosed in WO 2009/072006.

Figure 8A:
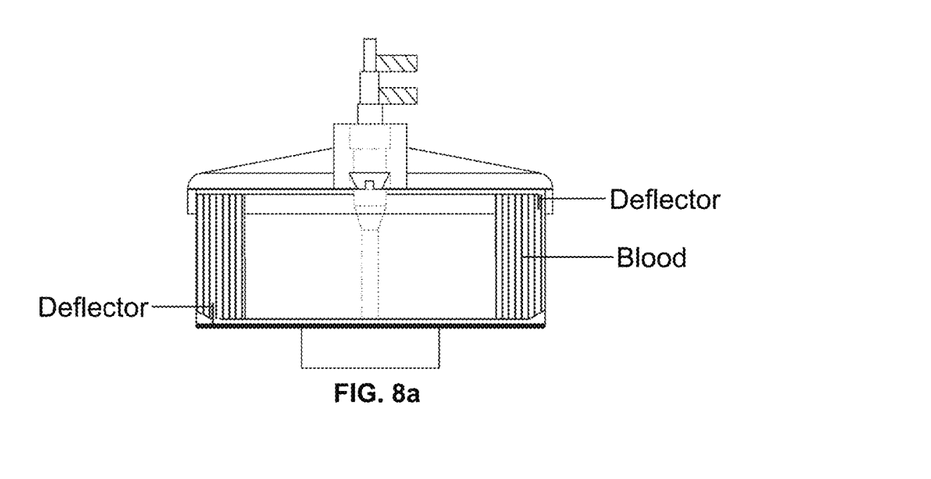
FIGS. 8a, 8b show an example of use of the present chamber.

1. Example Cell Separation Process 250 ml blood were introduced into the chamber with deflectors and subjected to a centrifugal force of 400×g (about 2500 rpm) for about 15 minutes as shown in FIG. 8a. Centrifugation of the sample resulted in the separation of the sample into layers, comprising leukocytes l, erythrocytes e, and plasma p, shown in FIG. 8b. During centrifugation, the layers can be observed in the chamber as rings, wherein the outer ring consists of the erythrocyte fraction. Leukocytes (including CD133+ cells) form a thin white ring adjacent to the erythrocyte layer. The inner ring consists of the yellow-coloured plasma fraction.

Figure 8B:
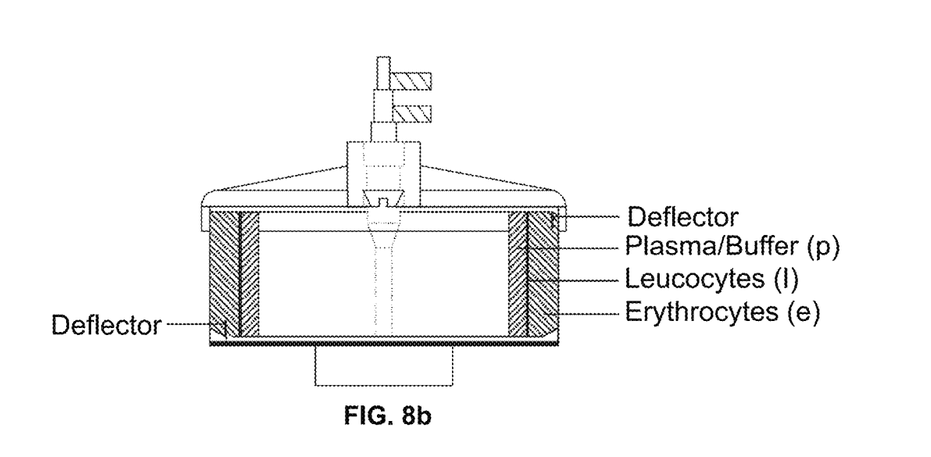

The outer layer e comprising erythrocytes was in part removed from the chamber via the top channel. Layer e was removed until the layer l comprising leukocytes reached the location between the opening of the bottom channel and the chamber wall. Then, the layer p comprising yellow-coloured plasma fraction was removed via the bottom channel into a container. After emptying the chamber, the layer l comprising leukocytes was washed several times with standard buffer. For this purpose, buffer is added to the chamber via the input port and centrifugation is started to separate the layers. Then, the inner layer comprising buffer is removed until the volume of the layer l comprising leukocytes is reduced to 70 ml and then the process is repeated (draining step).

Results

Figure 9:
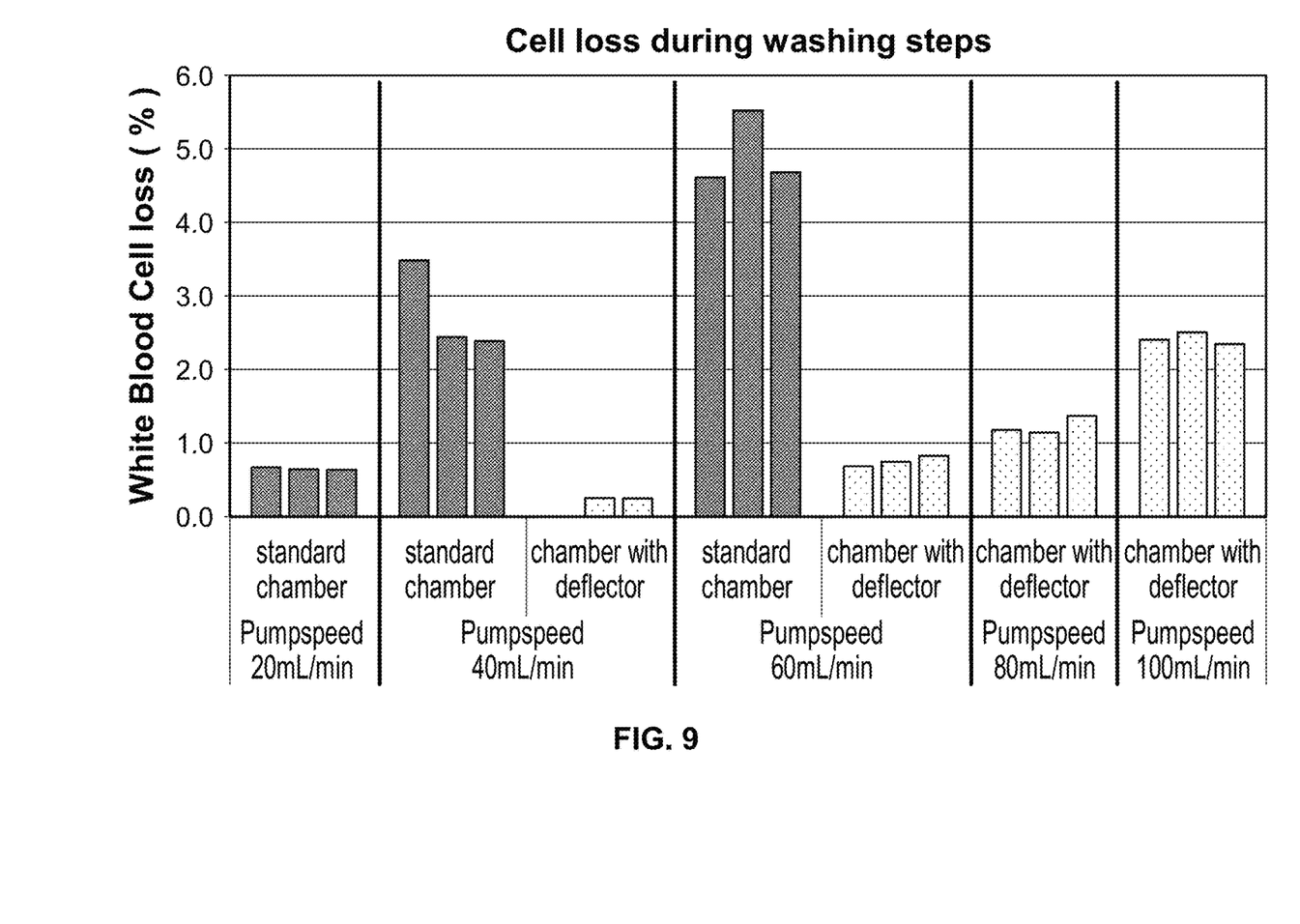
FIG. 9 shows graphically results of examples of use of the present chamber.

FIG. 9 shows a table with cell losses due to the draining of the inner layer comprising buffer (draining step) depending on the pump speed. For each pump speed, 3 experiments with the same sample were performed to rule out artifacts. The cell concentration was determined using an automated haematology analyser (e.g., the Sysmex KX-21N). With the standard centrifugation chamber, acceptable cell losses can only be obtained with very low pump speeds (left column). Such low pump speeds are not acceptable for cell separation for medical treatment purposes.

As can be seen from the second and third columns (from the left), higher pump speeds result in slightly higher cell losses for the chamber according to the invention (less than 1%), but up to 5% cell losses with the standard chamber. More than 2.5% loss of cells is not acceptable for medical treatment.

The first and second columns from the right show cell losses obtained under high pump speeds in a chamber according to the invention. Centrifugation chambers according to the invention allow a 4-fold increase of pump speeds resulting in a much faster processing time in comparison to a standard chamber with similar cell losses (compare the first and fourth column from the left).

In other words, centrifugation chambers with deflectors according to the present invention allow higher pump speeds with lesser loss of target cells.

2. Example Cell Washing Process

Cell washing was performed in a chamber according to the invention as described in Example 1 and a standard centrifugation chamber) with the same dimensions, ports, channels and openings as described above, but without deflectors.

Figure 10A:
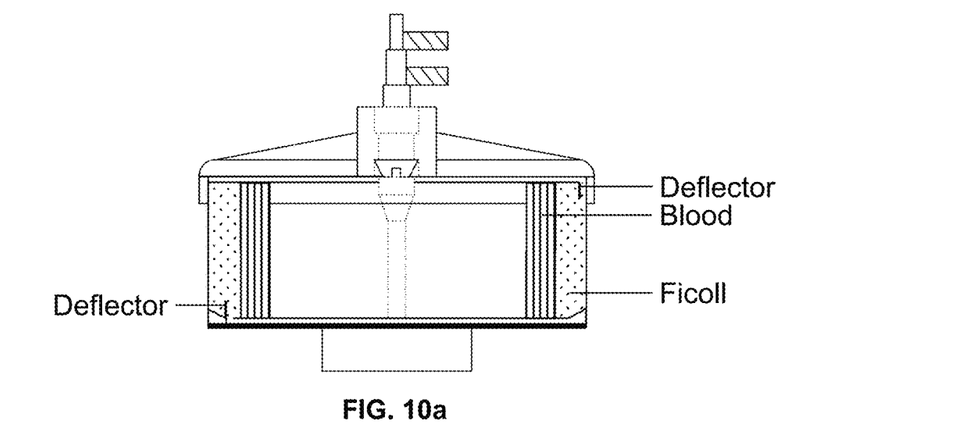
FIGS. 10a, 10b show yet another example.

In this example, the chamber according to the invention was used for density gradient centrifugation. 100 ml of blood and 100 ml of Ficoll were introduced into the chamber, resulting in two layers (see FIG. 10a) and subjected to a centrifugal force of 400×g (about 2500 rpm) for about 15 minutes. Centrifugation of the sample resulted in the separation of the sample into the layers comprising leukocytes l, erythrocytes/granulocytes e, Ficoll F and plasma p (see FIG. 10b). In the chamber, the layers are observed as rings, wherein the outer ring consists of the erythrocyte/granulocyte fraction followed (in the direction towards the axis assembly of the chamber) the Ficoll layer. Next, a thin white ring comprising leukocytes is observed. The inner ring consists of the yellow-coloured plasma fraction.

Figure 10B:
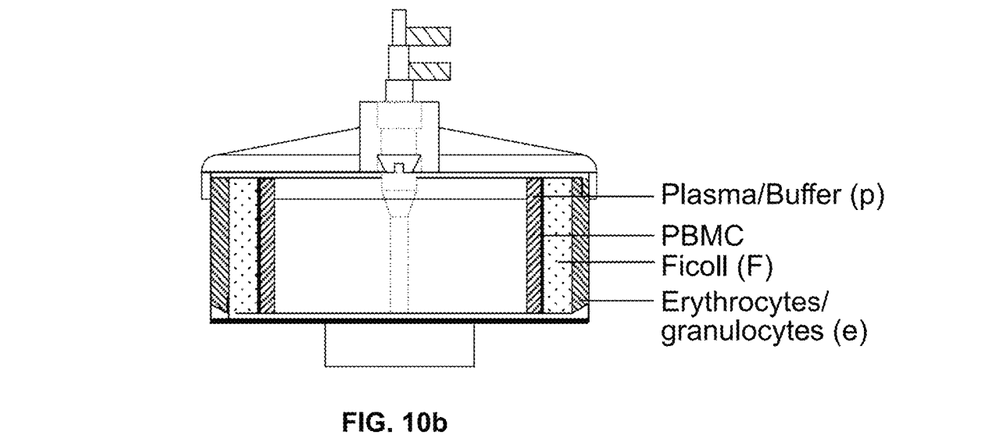

The (outer) layer e comprising erythrocytes and the Ficoll-Layer F was in part removed from the chamber via the top channel. The layers were removed until the layer comprising leukocytes reached the location of the opening of the bottom channel. Then, the layer comprising leukocytes was removed via the bottom channel into a reapplication container. After emptying the chamber, the layer comprising leukocytes was again introduced into the chamber and washed several times with standard buffer. For this purpose, buffer is added to the chamber via the input port and centrifugation is started to separate the layers. Then, the inner layer comprising buffer is removed until the volume of the layer (outer) comprising leukocytes is reduced to 70 ml. The process can be repeated several times.

It was found that the washing process in chamber according to the invention is about 4 times faster with same purity and/or cell losses than in a standard chamber, due to the faster draining speed of the washing liquids.

The invention claimed is:

1. A centrifuge chamber for separating a sample into components, comprising:
   a cylinder having a base plate and a cover plate; and
   a rotational axis assembly defining at least one port for input or output of the sample, the port being connected to a tube located on or in the base plate or cover plate and the tube having one or more openings into the centrifuge chamber;
   wherein at least one of the one or more openings of the tube has at least one flat-shaped deflector lying substantially parallel with the cylinder, wherein the at least one deflector has a base having a width of at most 1/10 of the inner circumference of the cylinder and an axial height that is the same or less than the width of the base of the at least one deflector, and wherein the at least one deflector is located on the tube between the at least one opening of the tube and the cylinder to shield the at least one opening and configured to reduce re-mixing during drainage.

2. The centrifuge chamber according to claim 1, wherein the at least one deflector is located between the at least one opening of the tube and the rotational axis assembly.

3. The centrifuge chamber according to claim 1, wherein the at least one deflector is located between the at least one opening of the tube and the rotational axis assembly, and further comprising a second deflector located between the at least one opening of the tube and the cylinder.

4. The centrifuge chamber according to claim 1, wherein the tube is located in the base plate or cover plate by a channel defined in the base plate or cover plate, the channel being covered by a cap.

5. The centrifuge chamber according to claim 4, wherein the deflector is attached to the cap.

6. The centrifuge chamber according to claim 4, wherein the openings are in the cap.

7. The centrifuge chamber according to claim 1, wherein the tube is a bore defined in the base plate or cover plate, and extending from outside of the base plate or cover plate to the rotational axis assembly.

8. The centrifuge chamber according to claim 1, wherein the cylinder carries on its outside surface at least one fin.

9. The centrifuge chamber according to claim 1, wherein the chamber defines venting holes in the base or cover plate, wherein the venting holes are connected via venting tubes in the rotational axis assembly to an inner volume of the chamber.

10. The centrifuge chamber according to claim 1, wherein the base plate or the cover plate has a mechanism that controls the sample separation.

11. The centrifuge chamber according to claim 1, wherein the cylinder has an elliptic shape with a diameter in a first dimension being 0.5 to 10% larger than in a second dimension oriented perpendicular to the first dimension.

12. The centrifuge chamber according to claim 11, wherein the tube is oriented in the larger dimension of the elliptic shape.

* * * * *